United States Patent
Ogino et al.

(10) Patent No.: US 6,541,632 B2
(45) Date of Patent: Apr. 1, 2003

(54) PROCESS FOR PRODUCING HETEROCYCLIC NITRILES

(75) Inventors: Hideaki Ogino, Niigata-ken (JP); Takashi Okawa, Niigata-ken (JP); Shuji Ebata, Niigata-ken (JP); Yoshinori Kanamori, Niigata-ken (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/173,619

(22) Filed: Jun. 19, 2002

(65) Prior Publication Data

US 2002/0151719 A1 Oct. 17, 2002

Related U.S. Application Data

(62) Division of application No. 09/613,632, filed on Jul. 11, 2000, now Pat. No. 6,429,330.

(30) Foreign Application Priority Data

Jul. 15, 1999 (JP) ............................................. 11-202234

(51) Int. Cl.⁷ ................... C07D 241/24; C07D 213/84; C07D 213/85
(52) U.S. Cl. .................. 544/336; 544/402; 546/145; 546/176; 546/246; 546/386; 548/202; 548/236; 548/335.1; 548/375.1; 548/505; 548/561; 549/61; 549/426; 549/474
(58) Field of Search ................................ 544/336, 402; 546/145, 176, 246, 386; 548/202, 236, 335.1, 375.1, 505, 561; 549/61, 426, 474

(56) References Cited

U.S. PATENT DOCUMENTS

| | | | |
|---|---|---|---|
| 3,803,204 A | 4/1974 | Grasselli et al. ............ | 558/329 |
| 4,044,042 A | 8/1977 | Angstadt ..................... | 558/328 |
| 4,284,781 A | 8/1981 | Sze .............................. | 546/286 |
| 4,814,479 A | 3/1989 | Engelbach et al. .......... | 558/328 |
| 4,883,897 A | 11/1989 | Kiyomiya et al. ........... | 558/327 |
| 5,235,088 A | 8/1993 | Paparizos et al. ........... | 558/324 |
| 6,107,510 A | 8/2000 | Ebata et al. ................. | 558/327 |
| 6,187,943 B1 | 2/2001 | Sasaki et al. ................ | 558/318 |

FOREIGN PATENT DOCUMENTS

| | | |
|---|---|---|
| JP | 49-13141 | 2/1974 |
| JP | 49-45860 | 12/1974 |
| JP | 63-190646 | 8/1988 |
| JP | 1-275551 | 11/1989 |
| JP | 5-170724 | 7/1993 |
| JP | 9-71561 | 3/1997 |
| JP | 10-120641 | 5/1998 |

OTHER PUBLICATIONS

Database WPI, Section Ch, Week 199532, AN 19995–242657, Derwent Publications Ltd., Sumitomo Chemical Co., Ltd., Jun. 6, 1995.

*Primary Examiner*—Bernard Dentz
(74) *Attorney, Agent, or Firm*—Antonelli, Terry, Stout & Kraus, LLP

(57) ABSTRACT

A carbocyclic or heterocyclic compound, ammonia and an oxygen-containing gas are subjected to fluid catalytic reaction in vapor phase in the presence of a catalyst containing alkali metal to produce an aromatic or heterocyclic nitrile. The use of the catalyst containing a specific amount of alkali metal enables the stable production of the aromatic or heterocyclic nitrile in high yields with little change with time even when water is present in the reaction system. The use of the catalyst containing the alkali metal also enables the recycle and reuse of unreacted ammonia which is usually accompanied by water, thereby reducing production costs.

18 Claims, No Drawings

PROCESS FOR PRODUCING HETEROCYCLIC NITRILES

This application is a Divisional application of application Ser. No. 09/613,632, filed Jul. 11, 2000 now U.S. Pat. No. 6,429,330, the contents of which are incorporated herein by reference in their entirety.

BACKGROUND OF THE INVENTION

1. Field of the Invention

The present invention relates to a process for producing nitrile compounds by reacting carbocyclic or heterocyclic compounds with a mixed gas of ammonia and oxygen.

2. Description of the Prior Art

Aromatic nitrites produced by ammoxidation of carbocyclic compounds are useful as raw materials for manufacturing synthetic resins, agricultural chemicals, etc., and as intermediate materials for producing amines, isocyanates, etc. Heterocyclic nitrites produced by ammoxidation of heterocyclic compounds are also useful as intermediates of medicines, animal feed additives, food additives, etc.

Ammoxidation of carbocyclic or heterocyclic compounds to aromatic or heterocyclic nitrile compounds generates a larger amount of heat as compared to ammoxidation of olefins. Therefore, a vapor-phase fluid catalytic reaction has been advantageously used for the ammoxidation of carbocyclic or heterocyclic compounds because the heat of reaction can be easily removed and side reactions due to local heating can be avoided. Various catalyst systems comprising a metal oxide or comprising a metal oxide supported on a carrier such as silica and alumina have been proposed for use in the vapor-phase fluid catalytic reaction.

For instance, Japanese Patent Publication No. 49-45860 produces an aromatic nitrile by ammoxidation of an alkyl-substituted aromatic compound in the presence of a catalyst containing V, Cr and B. Japanese Patent Application Laid-Open No. 49-13141 conducts the similar reaction in the presence of a catalyst containing Fe, Bi and Mo. Japanese Patent Application Laid-Open No. 63-190646 discloses ammoxidation of an alkyl-substituted aromatic compound or an alkyl-substituted alicyclic compound using an Fe—Sb catalyst.

Japanese Patent Application Laid-Open No. 1-275551 discloses ammoxidation of an alkyl-substituted aromatic compound or an alkyl-substituted heterocyclic compound in the presence of a V—Cr—B—Mo catalyst. Japanese Patent Application Laid-Open No. 5-170724 conducts the similar reaction in the presence of an Mo—P catalyst. Japanese Patent Application Laid-Open No. 9-71561 produces dicyanobenzene by ammoxidation of xylene in the presence of an Fe—Sb—V catalyst.

These known processes are advantageous because aromatic or heterocyclic nitrites are produced in high yields. However, the catalysts used in the processes are decreased in their activity with time. Therefore, it has been demanded to produce nitrite compounds in high yields over a long period of time. To meet the demands, there have been proposed a method for inhibiting the catalyst deterioration in fluidized reaction, a catalyst with little activity change with time, etc. For instance, Japanese Patent Application Laid-Open No. 10-120641 teaches to prevent the deterioration of a metal oxide catalyst containing V and/or Mo by a controlled feeding of raw materials to a fluid reactor.

As described above, in the process for producing nitrile compounds by fluid catalytic ammoxidation of carbocyclic or heterocyclic compounds in vapor-phase, various attempts have been made to improve catalysts and apparatuses for preventing deterioration of the catalysts. However, it is still demanded to produce the nitrite compounds stably in high yields over a prolonged period of time.

SUMMARY OF THE INVENTION

It is an object of the present invention to provide an economical process for producing a nitrite compound by vapor-phase fluid catalytic reaction of a carbocyclic or heterocyclic compound with ammonia and an oxygen-containing gas in high yields with little lowering with time over a long period of time.

As a result of extensive researches and studies on the production of nitrile compounds in view of the above objects, the inventors have found that one of the attributing causes of the deterioration of catalyst activity is water accompanying unreacted ammonia during its recycle and reuse, and that the use of catalysts containing a specific amount of alkali metal enables the ammoxidation to be stably performed with little change with time in the yields over a long period of time. The present invention has been accomplished based on this finding.

Namely, in accordance with the present invention, there is provided a process for producing an aromatic or heterocyclic nitrile, comprising a step of subjecting a carbocyclic or heterocyclic compound, ammonia and an oxygen-containing gas to fluid catalytic reaction in vapor phase in the presence of a catalyst containing 0.10 to 0.40% by weight of alkali metal; and a step of recycling unreacted ammonia recovered from a reaction product gas.

DETAILED DESCRIPTION OF THE INVENTION

The present invention will be described in detail below.

In the vapor-phase catalytic reaction of the present invention, a carbocyclic compound or a heterocyclic compound is reacted with an oxygen-containing gas and ammonia. To effectively remove heat of reaction and avoid side reactions due to local heating, the catalytic reaction is carried out in fluidized manner.

The carbocyclic compounds used as raw materials in the present invention has a carbon ring selected from the group consisting of benzene, naphthalene, anthracene, cyclohexene, cyclohexane, dihydronaphthalene, tetralin and decaline. The carbon ring has at least one nitrile-forming group selected from the group consisting of methyl, ethyl, propyl, formyl, acetyl, hydroxymethyl and methoxycarbonyl. Further, the carbocyclic compound may have another substituent such as halogen atom, hydroxyl, alkoxyl, amino, nitro, etc. Examples of the carbocyclic compounds include toluene, xylene, trimethylbenzene, ethylbenzene, methylnaphthalene, dimethylnaphthalene, methyltetralin, dimethyltetralin, chlorotoluene, dichlorotoluene, methylaniline, cresol and methylanisole.

The heterocyclic compounds used in the present invention have at least one hetero ring selected from the group consisting of furan, pyrrole, indole, thiophene, pyrazole, imidazole, oxazole, pyran, pyridine, quinoline, isoquinoline, pyrroline, pyrrolidine, imidazoline, imidazolidine, piperidine and piperazine. The hetero ring has at least one nitrile-forming group selected from the same group as described above for the carbocyclic compounds. Examples of the heterocyclic compounds include furfural, 2-methylthiophene, 3-methylthiophene, 2-formylthiophene, 4-methylthiazole, methylpyridine, dimethylpyridine, trimethylpyridine, methylquinoline, methylpyrazine, dimethylpyrazine and methylpiperazine.

The ammonia used as a raw material in the present invention may be of industrial grade. The amount of ammonia used is 1.5 to 10 moles, preferably 3 to 5 moles per one mole of the nitrile-forming group in the carbocyclic or heterocyclic compound. When the amount of ammonia used is less than the above range, the yield of the nitrile compound is lowered. When the amount of ammonia used exceeds the above range, the space time yield of the nitrile compound becomes small.

In the process of the present invention, the unreacted ammonia in reaction product gas is recovered and recycled to the reaction system for reuse. The method of recovering the unreacted ammonia from the reaction product gas is not particularly restricted. From an industrial viewpoint, it is suitable that the unreacted ammonia is absorbed in water, and then separated from by-products by distillation. The oxygen-containing gas used in the present invention may be usually air. Alternatively, diluted air or oxygen with an inert gas such as nitrogen, carbon dioxide or waste gases may also be used as the oxygen-containing gas. The oxygen concentration in the oxygen-containing gas is preferably 10 to 20% by volume. The amount of oxygen used is 1.5 moles or larger, preferably 2 to 50 moles per one mole of the nitrile-forming group in the carbocyclic or heterocyclic compound. When less than the above range, the yield of the nitrile compound is lowered. When exceeding the above range, the space time yield of the nitrile compound becomes small.

The catalyst used in the present invention contains an alkali metal in an amount of 0.1 to 0.4% by weight, preferably 0.1 to 0.3% by weight based on the weight of a supported catalyst (total weight of the catalyst and carrier).

When the content of the alkali metal is less than the above range, the catalyst is poor in mechanical strength such as wear resistance (attrition resistance). When the content exceeds the above range, the sintering of the catalyst proceeds by interaction between water in the raw materials and the alkali metal in the catalyst, resulting in the reduction with time of yields of the nitrile compound.

The process of the present invention is preferably performed in the presence of a catalyst comprising at least one oxide selected from the group consisting of oxides of V, Mo and Fe.

In addition to the oxides of V, Mo and Fe, the catalyst may further contain at least one oxide selected from the group consisting of oxides of Mg, Ca, Ba, La, Ti, Zr, Cr, W, Co, Ni, B, Al, Ge, Sn, Pb, P, Sb and Bi. Such a catalyst is represented by the formula:

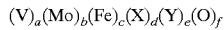

$(V)_a(Mo)_b(Fe)_c(X)_d(Y)_e(O)_f$ wherein X is at least one element selected from the group consisting of Mg, Ca, Ba, La, Ti, Zr, Cr, W, Co and Ni; Y is at least one element selected from the group consisting of B, Al, Ge, Sn, Pb, P, Sb and Bi; and subscripts a, b, c, d and e represent atomic proportions, a being 0.01 to 1, preferably 0.1 to 0.7; b being 0.01 to 1, preferably 0.05 to 0.7; c being 0 to 1, preferably 0.05 to 0.7; d being 0 to 1, preferably 0.05 to 0.7; e being 0 to 1, preferably 0.05 to 0.7 and f being the number of oxide-forming oxygen atoms.

Of the metal oxide catalysts, preferred are V—Cr—B—Mo—P—(Na and/or K) metal oxide catalysts. Examples of the vanadium sources may be inorganic salts of vanadium such as ammonium salts and sulfates, and vanadium salts of organic acids such as oxalic acid and tartaric acid. Examples of the molybdenum sources may be ammonium molybdate, phosphomolybdic acid, ammonium phosphomolybdate and molybdenum salts of organic acids such as oxalic acid and tartaric acid. Examples of the chromium sources may be chromic acid, nitrates of chromium, hydroxides of chromium, ammonium chromate, ammonium dichromate, and chromium salts of organic acids such as oxalic acid and tartaric acid. Examples of the boron sources may be boric acid, ammonium borate, etc. The alkali metal may be Li, Na, K, Rb and Cs, and Na and K are preferable. Examples of the alkali metal sources may be alkali hydroxides, alkali carbonates, alkali nitrates and alkali salts of organic acids such as oxalic acid, tartaric acid and acetic acid. The sources for other metals may be metal salts of inorganic or organic acids, which are easily converted into metal oxides by heating in air.

The metal oxide catalysts are preferably supported on known carrier such as silica, alumina, etc., and preferably silica. Examples of silica used as the carrier include silica gel, colloidal silica, anhydrous silica,. etc. as described, for example, in "Chemical Handbook, Applied Chemistry 1" published by Maruzen (1986), pp. 256–258. The amount of alkali metal contained in the silica carrier should be considered in preparing a supported catalyst so that the alkali metal content falls within the range specified above. The amount of the carrier used is 20 to 80% by weight, preferably 40 to 70% by weight based on the weight of the supported catalyst.

The catalyst used in the present invention can be produced by known methods. For instance, the preparation of a supported catalyst comprising a silica carrier supporting V—Cr—B—Mo—P—Na oxide catalyst is described below. An aqueous boric acid solution, sodium acetate and silica sol are successively added to an oxalic acid solution dissolving vanadium oxide and chromium oxide, thereby obtaining a slurry. A dissolving assistant such as polyhydric alcohols, α-monocarboxylic acids and dioxycarboxylic acids may be added, if desired, to facilitate the dissolution of boric acid. The slurry is sprayed for drying and then further dried, if necessary, at 110 to 150° C. The dried slurry is calcined at 400 to 700° C., preferably 450 to 650° C. for several hours or longer in a stream of air. Prior to the calcination, the dried slurry is preferably precalcined at 200 to 400° C.

The catalyzed ammoxidation of the carbocyclic or heterocyclic compounds is carried out at 300 to 500° C., preferably 330 to 470° C. When the reaction temperature is lower than the above range, the conversion is low. When the reaction temperature is higher than the above range, the production of carbon dioxide, hydrogen cyanide, etc., is promoted, so that the yields of the aromatic or heterocyclic nitrites are reduced.

The reaction pressure is generally ordinary pressure. However, the reaction may be performed under increased or reduced pressure, if desired. The contact time between the reactant gas and the catalyst is usually in the range of 0.5 to 30 seconds, although varies depending upon kinds of raw materials, charged ratio between raw materials, air and ammonia, reaction temperature, etc.

In the present invention, the aromatic or heterocyclic nitriles may be collected by any known method, for example, by a method of cooling the reaction product gas to a temperature enough to precipitate the aromatic or heterocyclic nitrites, or a method of washing the reaction product gas with water or other suitable solvents.

Known catalysts do not undergo the deterioration with time in catalytic activity when water is not contained in the starting carbocyclic or heterocyclic compounds, oxygen-containing gas such as air and ammonia. However, when a non-negligible amount of water is contained, the sintering of the catalysts is promoted so that the catalyst activity is considerably deteriorated with time, thereby failing to stably produce the aromatic or heterocyclic nitrites.

Since the recovered ammonia contains a non-negligible amount of water, the catalyst activity is adversely affected by water. Although the water can be removed by distillation, adsorption, etc., these additional operations increase the production cost.

In the present invention, this problem in the prior art has been solved by the addition of alkali metal to the catalyst comprising oxides of V, Mo, Fe, etc. The addition of alkali metal maintains the catalyst strength such as wear resistance sufficiently high and prevents the deterioration of catalytic activity even when water enters into the reaction system accompanying the recycled ammonia, thereby stably producing the aromatic or heterocyclic nitrites at high yields over a long period of time.

The present invention will be described in more detail by reference to the following examples and comparative examples. However, it should be noted that the following examples are not intended to limit the invention thereto.

EXAMPLE 1
(Preparation of Catalyst)

A mixture of 229 g of vanadium pentoxide ($V_2O_5$) and 500 ml of water was heated to 80 to 90° C., and then, 477 g of oxalic acid were dissolved therein under vigorous stirring. Separately, a mixture of 963 g of oxalic acid and 400 ml of water was heated to 50 to 60° C., and then, a solution of 252 g of chromic anhydride ($CrO_3$) in 200 ml of water was dissolved therein under vigorous stirring. The vanadyl oxalate solution and the chromium oxalate solution thus prepared were mixed with each other at 50 to 60° C. to obtain a vanadium-chromium solution, to which were successively added a solution of 41.1 g of phosphomolybdic acid ($H_3[PMo_{12}O_{40}] \cdot 20H_2O$) in 100 ml of water and a solution of 4.0 g of potassium acetate ($CH_3COOK$) in 100 ml of water. To the resultant solution, were added 2,500 g of 20 wt. % aqueous silica sol (containing 0.02% by weight of $Na_2O$) to obtain a slurry, to which 78 g of boric acid ($H_3BO_3$) were added. The slurry was heated and concentrated until the weight was reduced to about 3,800 g. The catalyst slurry thus prepared was spray-dried while maintaining the inlet temperature at 250° C. and the outlet temperature at 130° C. The spray-died catalyst was further dried in a dryer at 130° C. for 12 hours, pre-calcined at 400° C. for 0.5 hour, and then calcined under air flow at 550°0 C. for 8 hours. The supported catalyst thus prepared had an alkali metal content of 0.21% by weight, an atomic ratio of V:Cr:B Mo:P:Na:K=1:1:0.5:0.086:0.007:0.009:0.020 and a catalyst concentration of 50% by weight.

(Test of Catalyst Strength)

Into a test tube (38 mm inner diameter) provided at an upper portion thereof with a collecting thimble (No. 84, produced by Toyo Roshi Co., Ltd.), 50 g of the supported catalyst prepared above were charged. Air was then introduced into the test tube at a feed rate of 312 m/sec at room temperature to fluidize the supported catalyst for 20 hours. The amount of the worn-out catalyst particles scattered into the collecting thimble during the fluidization was 2.1% by weight based on the charged amount. This shows that the supported catalyst had a mechanical strength sufficient for practical use.

(Test of Catalytic Activity)

Into a reactor (23 mm inner diameter) heated by a resistance heat generator, 40 ml of the supported catalyst were charged. A water-free mixed gas comprising 3.2% by volume of m-xylene, 25.3% by volume of ammonia and 71.5% by volume of air, or a mixed gas further containing, in addition to the above components, water in an amount of 20.0% by volume based on ammonia was introduced into the reactor and subjected to fluid catalytic ammoxidation at 420° C. at which the supported catalyst gave the maximum yield of isophthalonitrile and at a hourly space velocity (SV) of 850 $hr^{-1}$. The actual yields of isophthalonitrile based on m-xylene were 86.5 mol % when using the water-free mixed gas, and 86.1 mol % when using the water-containing mixed gas. After the heat load of 450° C.×300 hours, the fluid catalytic ammoxidation was repeated at 420° C. As a result, the yields of isophthalonitrile based on m-xylene were 86.1 mol % for the water-free mixed gas, and 85.8 mol % for the water-containing mixed gas. As seen from the results, isophthalonitrile was stably produced in high yields with little lowering with time even when the mixed gas contained water.

EXAMPLE 2

The same procedures of the activity test as in Example 1 were repeated using the supported catalyst prepared in Example 1 except that 3-methylpyridine was used instead of m-xylene. Specifically, a water-free mixed gas comprising 2.6% by volume of 3-methylpyridine, 11.5% by volume of ammonia and 85.9% by volume of air, or a mixed gas further containing, in addition to the above components, water in an amount of 19.0% by volume based on ammonia, was introduced into the reactor, and the fluid catalytic ammoxidation was carried out at 390° C. at which the maximum yield of 3-cyanopyridine was attained and at a hourly space velocity (SV) of 810 $hr^{-1}$. The yield of 3-cyanopyridine based on 3-methylpyridine was 89.5 mol % when using the water-free mixed gas, and 89.3 mol % when using the water-containing mixed gas. After the heat load of 450° C.×300 hours, the ammoxidation was repeated at 390° C. The yield of 3-cyanopyridine based on 3-methylpyridine was 89.3 mol % when using the water-free mixed gas, and 89.0 mol % when using the water-containing mixed gas. As seen from the results, 3-cyanopyridine was stably produced in high yields with little lowering with time even when the mixed gas contained water.

EXAMPLE 3

The same procedures of the activity test as in Example 1 were repeated using the supported catalyst prepared in Example 1 except that the fluid catalytic ammoxidation was conducted at 410° C. and p-xylene was used instead of m-xylene. The yield of terephthalonitrile based on p-xylene was 88.3 mol % when using the water-free mixed gas, and 88.0 mol % when using the water-containing mixed gas. After the heat load of 450° C.×300 hours, the reaction was repeated at 410° C. The yield of terephthalonitrile based on p-xylene was 87.8 mol % when using the water-free mixed gas, and 87.4 mol % when using the water-containing mixed gas. As seen from the results, terephthalonitrile was stably produced in high yields with little lowering with time even when the mixed gas contained water.

EXAMPLE 4
(Preparation of Catalyst)

A mixture of 700 ml of concentrated nitric acid and 900 ml of water was heated to 50 to 60° C., and then, 92 g of electrolytic iron was dissolved therein little by little. The solution was further added with 1,460 g of 20 wt. % aqueous silica sol (containing 0.02% by weight of $Na_2O$) to obtain a slurry, to which 359 g of diantimony trioxide ($Sb_2O_3$), 19 g of phosphoric acid ($H_3PO_4$) and a solution of 2.53 g of potassium acetate ($CH_3COOK$) in 100 ml of water were dissolved under mixing. After adjusting the pH to 2 by 15% aqueous ammonia, the resultant slurry mixture was aged at 100° C. for 3 hours. The slurry was further mixed with a chromium solution of 33 g of chromium nitrate nonahydrate ($Cr(NO_3)_3.9H_2O$) in 400 ml of water. Separately, a mixture of 60 g of vanadium pentoxide ($V_2O_5$) and 130 ml of water was heated to 80 to 90° C., and then, 125 g of oxalic acid were dissolved therein under vigorous stirring, thereby preparing a vanadyl oxalate solution. The vanadyl oxalate solution was mixed with the slurry under vigorous stirring to prepare a catalyst slurry, which was then spray-dried while maintaining an inlet temperature at 250° C. and an outlet temperature at 130° C. The spray-dried catalyst was further dried in a dryer at 130° C. for 12 hours, pre-calcined at 400° C. for 0.5 hour, and then calcined under air flow at 800° C. for 8 hours. The resultant supported catalyst had an alkali metal content of 0.21% by weight, an atomic ratio of Fe:Sb:V:Cr:P:Na:K=1:0.7:0.4:0.25:0.77:0.011:0.031 and a catalyst concentration of 50% by weight.

(Test of Catalyst Strength)

The same procedures of the strength test as in Example 1 were repeated on the supported catalyst prepared above. The supported catalyst was fluidized for 20 hours. As a result, the amount of the worn-out catalyst particles scattered into the collecting thimble was 2.6% by weight based on the charged amount. This shows that the supported catalyst had a mechanical strength sufficient for practical use.

(Test of Catalytic Activity)

The same procedures of the activity test as in Example 1 were repeated except that the fluid catalytic ammoxidation was performed at 440° C. using the above supported catalyst. The yield of isophthalonitrile based on m-xylene was 78.5 mol % when using the water-free mixed gas, and 77.5 mol % when using the water-containing mixed gas. After the heat load of 450° C.×300 hours, the reaction was repeated at 440° C. The yield of isophthalonitrile based on m-xylene was 78.4 mol % when using the water-free mixed gas, and 77.5 mol % when using the water-containing mixed gas. As seen from the results, isophthalonitrile was stably produced in high yields with little lowering with time even when the mixed gas contained water.

Comparative Example 1

(Preparation of Catalyst)

The same procedures for the preparation of catalyst as in Example 1 were repeated except that 3.0 g of potassium acetate ($CH_3COOK$) were used. The resultant supported catalyst had an alkali metal content of 0.48% by weight, an atomic ratio of V:Cr:B:Mo:P:Na:K= 1:1:0.5:0.086:0.007:0.064:0.012, and a catalyst concentration of 50% by weight.

(Test of Catalyst Strength)

The same procedures of the strength test as in Example 1 were repeated on the above supported catalyst. The supported catalyst was fluidized for 20 hours. As a result, the amount of the worn-out catalyst particle scattered into the collecting thimble was 1.7% by weight based on the charged amount. This shows that the supported catalyst had a mechanical strength sufficient for practical use.

(Test of Catalytic Activity)

The same procedures of the activity test as in Example 1 were repeated except that the fluid catalytic ammoxidation was performed at 420° C. using the above supported catalyst. The yield of isophthalonitrile based on m-xylene was 86.9 mol % when using the water-free mixed gas, and 86.8 mol % when using the water-containing mixed gas. After the heat load of 450° C.×300 hours, the reaction was repeated at 420° C. As a result, the yield of isophthalonitrile based on m-xylene was 86.6 mol % when using the water-free mixed gas, and 80.7 mol % when using the water-containing mixed gas. As seen from the results, isophthalonitrile was stably produced in high yields with little lowering with time even when the mixed gas contained water.

Comparative Example 2

(Preparation of Catalyst)

The same procedures for the preparation of catalyst as in Example 1 were repeated except that no potassium acetate ($CH_3COOK$) was used. The resultant supported catalyst had an alkali metal content of 0.04% by weight, an atomic ratio of V:Cr:B:Mo:P:Na=1:1:0.5:0.1:0.086:0.004, and a catalyst concentration of 50% by weight.

(Test of Catalyst Strength)

The same procedures of the strength test as in Example 1 were repeated on the above supported catalyst. The supported catalyst was fluidized for 20 hours. As a result. the amount of the worn-out catalyst particles scattered into the collecting thimble was 7.8% by weight based on the charged amount. This indicates that the supported catalyst had a poor strength and not suitable for practical use.

Comparative Example 3

In the same manner as in Example 2, the fluid catalytic ammoxidation was repeated at 390° C. except that 3-methylpyridine was used instead of m-xylene using the supported catalyst prepared in Comparative Example 1. The yield of 3-cyanopyridine based on 3-methylpyridine was 89.8 mol % when using the water-free mixed gas, and 89.5 mol % when using the water-containing mixed gas. After the heat load of 450° C.×300 hours, the reaction was repeated at 390° C. As a result, the yield of 3-cyanopyridine based on 3-methylpyridine was 89.7 mol % when using the water-free mixed gas. The yield when using the water-containing mixed gas drastically lowered to 80.2 mol %. As seen from the results, the comparative catalyst failed to stably produce 3-methylpyridine due to significant lowering with time of the yield.

Comparative Example 4

(Preparation of Catalyst)

The same procedures for the preparation of catalyst as in Example 4 were repeated except that 6.49 g of potassium acetate ($CH_3COOK$) was used. The resultant supported catalyst had an alkali metal content of 0.48% by weight, an atomic ratio of Fe:Sb:V:Cr:B:Na:K= 1:1.5:0.4:0.5:0.77:0.011:0.081, and a catalyst concentration of 50% by weight.

(Test of Catalyst Strength)

The same procedures of the strength test as in Example 1 were repeated on the above supported catalyst. The supported catalyst was fluidized for 20 hours. As a result, the amount of the worn-out catalyst scattered into the collecting thimble was 2.4% by weight based on the charged amount. This indicates that the supported catalyst had a mechanical strength sufficient for practical use.

(Test of Catalytic Activity)

The same procedures of the activity test as in Example 1 were repeated except that the fluid catalytic ammoxidation was performed at 440° C. using the above supported catalyst. The yield of isophthalonitrile based on m-xylene was 79.1 mol % when using the water-free mixed gas, and 78.0 mol % when using the water-containing mixed gas. After the heat load of 450° C.×300 hours, the reaction was repeated at 440° C. As a result, the yield of isophthalonitrile based on m-xylene was 78.5 mol % when using the water-free mixed gas. The yield when using the water-containing mixed gas drastically lowered to 72.4 mol %. As seen from the results, the comparative catalyst failed to stably produce isophthalonitrile due to significant lowering with time of the yield.

Comparative Example 5
(Preparation of Catalyst)

The same procedures for the preparation of catalyst as in Example 1 were repeated except that no potassium acetate ($CH_3COOK$) was used. The resultant supported catalyst had an alkali metal content of 0.04% by weight, an atomic ratio of Fe:Sb:V:Cr:B:Na=1:1.5:0.4:0.5:0.77:0.011, and a catalyst concentration of 50% by weight.
(Test of Catalyst Strength)

The same procedures of the strength test as in Example 4 were repeated on the above supported catalyst. The supported catalyst was fluidized for 20 hours. As a result, the amount of the worn-out catalyst scattered into the collecting thimble was as large as 9.2% by weight based on the charged amount. This indicates that the mechanical strength of the supported catalyst was so poor for practical use.

As is apparent from the above examples, the catalyst containing a specific amount of alkali metal enables the stable production of aromatic nitrites or heterocyclic nitriles in high yields with little change with time by vapor-phase fluid catalytic ammoxidation of carbocyclic or heterocyclic compounds, because the catalytic activity is not deteriorated by water in the recycled unreacted ammonia recovered from the reaction product gas.

Accordingly, aromatic nitriles or heterocyclic nitrites are produced in industrially advantageous manner. Thus, the present invention has a large industrial value.

What is claimed is:

1. A process for producing a heterocyclic nitrile, comprising:
    subjecting a heterocyclic compound, ammonia and an oxygen-containing gas to fluid catalytic reaction in vapor phase in the presence of a catalyst containing 0.1 to 0.4% by weight of alkali metal to produce the heterocyclic nitrile; and
    recycling unreacted ammonia recovered from a reaction product gas from the fluid catalytic reaction in vapor phase.

2. The process according to claim 1, wherein the catalyst further contains at least one oxide selected from the group consisting of oxides of V, Mo and Fe.

3. The process according to claim 2, wherein the catalyst further contains at least one oxide selected from the group consisting of oxides of Mg, Ca, Ba, La, Ti, Zr, Cr, W, Co, Ni, B, Al, Ge, Sn, Pb, P, Sb and Bi.

4. The process according to claim 3, wherein the catalyst is supported on silica.

5. The process according to claim 3, wherein the oxide component of the catalyst is represented by the following formula:

$$(V)_a(MO)_b(Fe)_c(X)_d(Y)_e(O)_f$$

wherein X is at least one element selected from the group consisting of Mg, Ca, Ba, La, Ti, Zr, Cr, W, Co and Ni; Y is at least one element selected from the group consisting of B, Al, Ge, Sn, Pb, P, Sb and Bi; and subscripts a, b, c, d, e and f represent atomic proportions, a being 0.01 to 1; b being 0.01 to 1; c being 0 to 1; d being 0 to 1; e being 0 to 1 and f being the number of oxide-forming oxygen atoms.

6. The process according to claim 1, wherein the fluid catalytic reaction in vapor phase is carried out in the presence of a supported catalyst comprising silica supporting a catalyst containing the alkali metal and oxides of V, Cr, B, Mo and P.

7. The process according to claim 1, wherein the alkali metal is Na and/or K.

8. The process according to claim 1, wherein the heterocyclic compound has a hetero ring substituted by at least one nitrile-forming group.

9. The process according to claim 8, wherein the nitrile-forming group is selected from the group consisting of methyl, ethyl, propyl, formyl, acetyl, hydroxymethyl and methoxycarbonyl.

10. The process according to claim 8, wherein the hetero ring is selected from the group consisting of furan, pyrrole, indole, thiophene, pyrazole, imidazole, oxazole, pyran, pyridine, quinoline, isoquinoline, pyrroline, pyrrolidine, imidazoline, imidazolidine, piperidine and piperazine.

11. The process according to claim 1, wherein the heterocyclic compound is selected from the group consisting of furfural, 2-methylthiophene, 3-methylthiophene, 2-formylthiophene, 4-methylthiazole, methylpyridine, dimethylpyridine, methylquinoline, methylpyrazine, dimethylpyrazine and methylpiperazine.

12. The process according to claim 1, wherein the ammonia is used in an amount of 1.5 to 10 moles per one mole of the nitrile-forming group in the heterocyclic compound.

13. The process according to claim 1, wherein the ammonia is used in an amount of 3 to 5 moles per one mole of the nitrile-forming group in the heterocyclic compound.

14. The process according to claim 1, wherein said fluid catalytic reaction is performed in the presence of a catalyst containing 0.1 to 0.3% by weight of alkali metal.

15. The process according to claim 14, wherein the alkali metal is selected from the group consisting of Na and K.

16. The process according to claim 1, wherein the alkali metal is selected from the group consisting of Li, Na, K, Rb and Cs.

17. The process according to claim 1, wherein the unreacted ammonia, recovered from the reaction gas product and recycled, includes water.

18. The process according to claim 1, wherein said recycling includes absorbing unreacted ammonia in water and separating the ammonia by distillation.

* * * * *